United States Patent [19]

Warriner

[11] Patent Number: Plant 6,518

[45] Date of Patent: Jan. 10, 1989

[54] ROSE PLANT JACUTE

[75] Inventor: William A. Warriner, Tustin, Calif.

[73] Assignee: Jackson & Perkins Company, Medford, Oreg.

[21] Appl. No.: 28,186

[22] Filed: Mar. 19, 1987

[51] Int. Cl.[4] ..... A01H 5/00
[52] U.S. Cl. ..... Plt./9
[58] Field of Search ..... Plt./9

*Primary Examiner*—James R. Feyrer
*Attorney, Agent, or Firm*—Majestic, Gallagher, Parsons & Siebert

[57] ABSTRACT

A rose variety of the miniature class is provided having an ability to root and grow rapidly to salable size in a four-inch pot, attractive hybrid tea form flowers of pink color, the occasional presence of seven sepals, over 100 petals per flower and resistance to powdery mildew.

1 Drawing Sheet

SUMMARY OF THE INVENTION

The present invention relates to a new and distinct variety of rose plant of the miniature class, which was originated by me by crossing an unnamed seedling with an unnamed seedling.

The primary objective of this breeding was to produce a new rose variety of the miniature class exhibiting long lasting pink flowers and suitable for pot growth. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Rapid compact growth;
2. Attractive pink hybrid tea form flowers;
3. Powdery mildew resistance;
4. Ease of rooting;
5. Up to seven sepals instead of five; and
6. Over 100 petals per flower.

Asexual reproduction of this new variety by cuttings, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacute". Color terminology is in accordance with The Royal Horticultural Society Colour Chart except where an ordinary dictionary significance for the color is apparent.

Observations of the buds and flowers were made from specimens grown in a greenhouse at Irvine, Calif. in October.

Flower

The blooming habit is continuous. The bud size is ¾ inches when the petals start to unfurl. The bud form is long, pointed ovoid. The bud color when sepals first divide is near Red 49A to Red 49B; when half blown, the upper side of petals is near Red 49A to Red 49B and the lower side of petals is near Red 49B. The sepals have a color near Green 138D. The surface texture is covered with fine hairs. There are three appendaged sepals lightly appendaged, and two unappendaged sepals with hairy edge. The receptacle color is near Green 138C of a funnel shape, small size and smooth surface. The peduncle is of short length, and smooth surface with occasional hairs. Peduncle color is light to medium green and the peduncle is stiff and short.

Bloom

Bloom size is small, with an average open size of one and one-half inches, borne in clusters. The clusters are rounded. The stems are strong and short. The form when first open is high center. This form then flattens and the outer petals curl back, quill fashion. Under normal conditions there are greater than 100 petals. The upper side of petals is near Red 49A to Red 49B, as is the reverse side of the petals. The base of petals has a small white to yellow half moon on both sides of each petal with the major color being near Red 49A to Red 49B. There are occasional pronounced white midribs down the back of outside petals. The general tonality at the end of the first day shows no change in color. At the end of the third day, there remains no discoloration.

The fragrance is slight. The petal texture is thin, of a deltoid shape with the tips being slightly recurved and edges moderately quilled.

The arrangement is imbricated with few petaloids in the center. The blooms drop off cleanly, and last on the plant for a long period and as a cut flower for a fair time.

Reproductive Parts

The anthers are small and few, of yellow color and tucked in calyx or partly so. The filaments are white, the pollen is lemon yellow, the styles are reddish, and the stigmas are lemon white.

Plant

A miniature bush of vigorous dwarf growth habit.

Foliage

Small size, normal in quantity. The new foliage is dark green with a bronze tint, and the old foliage is dark green. Normal mid-stem leaves have five leaflets.

The leaflets are of a broadly oval to oval, oval pointed shape, are glossy, and have a serrated edge. The serration is single and small in size. Petiole rachis is green and petiole underside is smooth. Stipules are medium and serrated. The foliage is resistant to mildew under normal growing conditions at Irvine, Calif.

Wood

New wood is light green, with a smooth bark. Old wood is green with a smooth bark.

Prickles

There are an ordinary number of prickles on main canes from the base and on laterals from the main canes. The form is medium and straight. Color when young is red.

Small Prickles

There are no small prickles on the main stalks or on the laterals.

Additional Distinguishing Traits

This novel rose plant has sepals which occasionally are seven in number with the extra two appearing to be originated from the petals.

Parentage

Both seed and pollen parents are unnamed seedlings.

Classification

Botanical is rosa hybrid and commercial is miniature.

I claim:

1. A new and distinct variety of rose plant and parts thereof of the miniature class substantially as herein shown and described, characterized particularly as to novelty by an ability to root and grow rapidly in a four-inch pot, attractive hybrid tea form flowers of pink color, the occasional presence of seven sepals, over 100 petals per flower and resistance to powdery mildew.

* * * * *

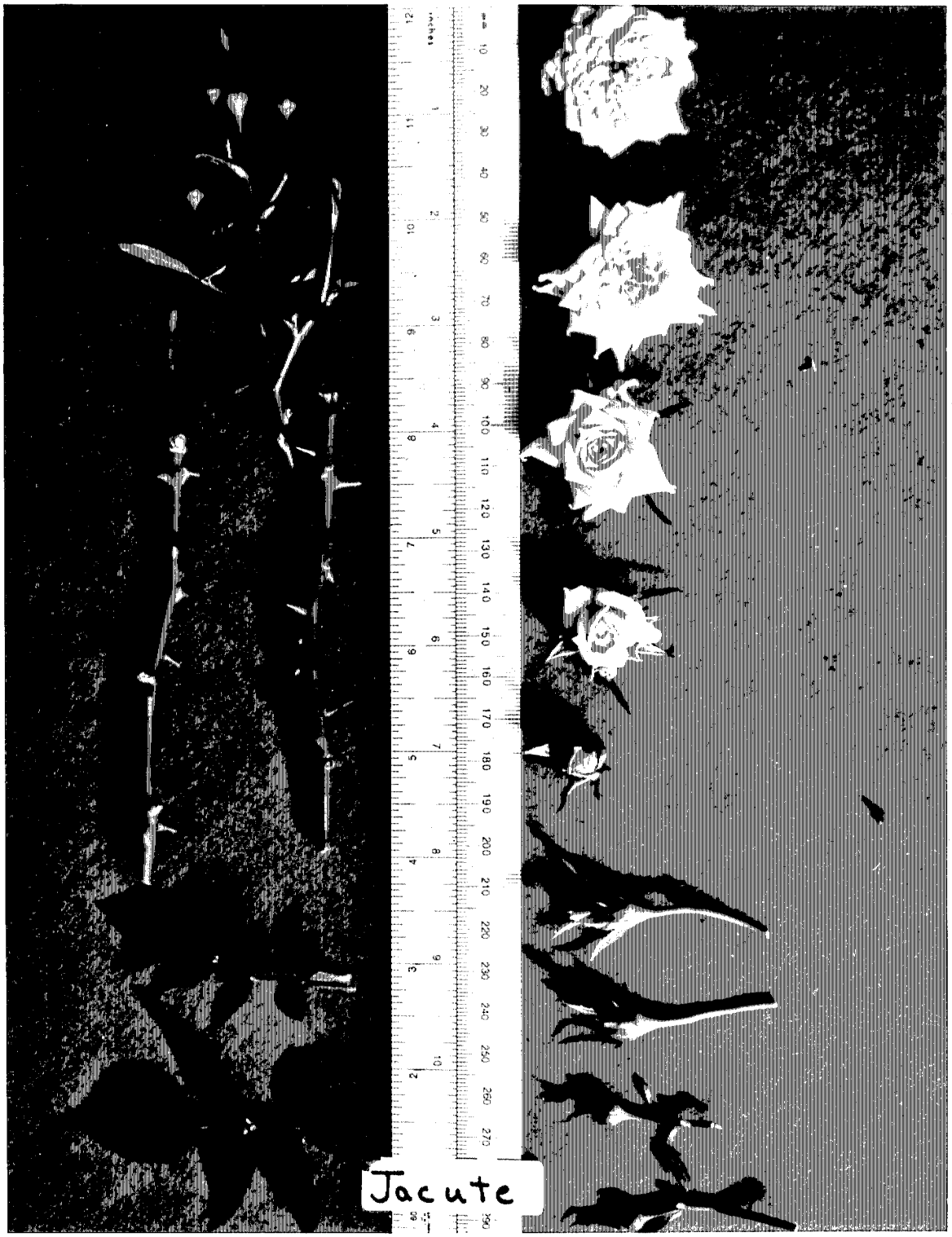
Jacute